(12) United States Patent
Schillinger et al.

(10) Patent No.: US 9,040,778 B2
(45) Date of Patent: May 26, 2015

(54) SOYBEAN CULTIVAR 131TD735

(71) Applicant: Schillinger Genetics, Inc, West Des Moines, IA (US)

(72) Inventors: John A. Schillinger, West Des Moines, IA (US); William K. Rhodes, Queenstown, MD (US)

(73) Assignee: Schillinger Genetics, Inc., West Des Moines, IA (US)

( * ) Notice: Subject to any disclaimer, the term of this patent is extended or adjusted under 35 U.S.C. 154(b) by 28 days.

(21) Appl. No.: 13/649,241

(22) Filed: Oct. 11, 2012

(65) Prior Publication Data

US 2014/0109255 A1 Apr. 17, 2014

(51) Int. Cl.
*A01H 4/00* (2006.01)
*A01H 5/00* (2006.01)
*A01H 5/10* (2006.01)
*C12N 15/82* (2006.01)

(52) U.S. Cl.
CPC ........................................ *A01H 5/10* (2013.01)

(58) Field of Classification Search
USPC .......................................................... 800/312
See application file for complete search history.

(56) References Cited

U.S. PATENT DOCUMENTS

2013/0198887 A1* 8/2013 Schillinger et al. ........... 800/263

OTHER PUBLICATIONS

Theodore Hymowitz, "The Kunitz Soybean Variety", www.aces.uiuc,edu/vista/html_pubs/irspsm91/kunitz.html (the date of this reference is not known, but the reference was known to the Applicant prior to the Applicant's effective filing date).

* cited by examiner

*Primary Examiner* — Cynthia Collins
(74) *Attorney, Agent, or Firm* — Ryan N. Carter; Glenn Johnson

(57) ABSTRACT

A soybean cultivar designated 131TD735 is disclosed. The invention relates to the seeds of soybean cultivar 131TD735, to the plants of soybean 131TD735, to plant parts of soybean cultivar 131TD735 and to methods for producing a soybean plant produced by crossing soybean cultivar 131TD735 with itself or with another soybean variety. The invention also relates to methods for producing a soybean plant containing in its genetic material one or more transgenes and to the transgenic soybean plants and plant parts produced by those methods. This invention also relates to soybean cultivars or breeding cultivars and plant parts derived from soybean cultivar 131TD735, to methods for producing other soybean cultivars, lines or plant parts derived from soybean cultivar 131TD735 and to the soybean plants, varieties, and their parts derived from use of those methods. The invention further relates to hybrid soybean seeds, plants and plant parts produced by crossing the cultivar 131TD735 with another soybean cultivar.

23 Claims, No Drawings

SOYBEAN CULTIVAR 131TD735

BACKGROUND

The present invention relates to a new and distinctive soybean cultivar, designated 131TD735.

The many developmental stages for developing useful and novel plant germplasm include, but are not necessarily limited to: study of the germplasm to ascertain the key traits associated therewith; selecting germplasm exhibiting traits consistent with the design goals of the breeding program; and engaging in plant breeding to obtain a variety that characterizes the desired traits and is stable.

Breeding methodology is dependent upon many variables. These variables include heritability, the genetic construct coding for the desired trait, and the commercial cultivar type.

Soybean breeding programs generally exist for the purpose of developing superior soybean cultivars that are both new and useful. The development of these new soybean cultivars requires the development and selection of soybean varieties exhibiting particular desired traits, and the crossing of these varieties and selection of superior hybrid crosses. Pedigree breeding methods, often used to improve self-pollinating plants, mutation breeding, mass and recurrent selection techniques, and backcross breeding techniques are a typical part of the soybean breeding program. As the generations advance, the plant breeder closely observes and selects for the desired phenotypes. Further, genotypical analysis is often employed to understand and advance the desired plant genotype, which analytical techniques may include: Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length polymorphisms (AFLPs), Simple Sequence Repeats (SSRs—which are also referred to as Microsatellites), and Single Nucleotide Polymorphisms (SNPs). These analytical techniques, generally referred to as molecular marker techniques, may be used to reconstruct a model or map the genetic structure in a process known as Quantitative Trait Loci (QTL) mapping. The purpose of the QTL mapping is to mark the alleles linked to the positive trait(s) and negative trait(s) so as to facilitate the enhancement of the positive trait(s) and the reduction of the undesired trait(s).

The various breeding methods are known to those skilled in this area, further, are disclosed in any number of references which include the following texts: Allard, 1960; Simmonds, 1979; Sneep et al., 1979; Fehr, 1987.

131TD735 is a soybean variety. Soybean, Glycine max (L), is a highly valuable crop and significant food source to the world. Also, the soybean is a valuable source of oil that may be used in edible ways or may be used as a feedstock for the production of fuels such as biodiesel or as lubricants. The goal of Applicant's soybean breeding program is to develop stable, high yielding soybean cultivars that are agronomically sound in light of the importance of this food source, energy source, or lubricant source. This goal is shown in soybean cultivar 131TD735, which further reflects development of a soybean variety with elevated protein levels valuable to all consumers.

SUMMARY

The following disclosures and related aspects pertaining to the invention are not limiting in scope. The description and examples provided herein disclose a new soybean cultivar designated 131TD735. This invention encompasses the seeds of soybean cultivar 131TD735, the plants of soybean cultivar 131TD735, and methods for producing a soybean plant produced by crossing the soybean cultivar 131TD735 with itself or another soybean cultivar, and the creation of variants by mutagenesis or transformation of soybean cultivar 131TD735.

In summary, the scope of this patent, and of the invention disclosed herein, covers (1) methods using the soybean cultivar 131TD735 including, but not limited to selfing, backcrosses, hybrid production, crosses to populations; and (2) plants produced using soybean cultivar 131TD735 as at least one parent, which parent may be used to produce first generation ($F_1$) soybean hybrid seeds and plants with superior characteristics.

Further included within the scope of the invention disclosed are single or multiple gene converted plants of soybean cultivar 131TD735, wherein the transferred gene(s) may be a dominant or recessive allele. Preferably, the transferred gene(s) confers agronomically useful traits such as herbicide resistance, insect resistance, resistance for bacterial, fungal, or viral disease, male fertility, male sterility, enhanced nutritional quality, and industrial usage. The transferred gene(s) may be a naturally occurring soybean gene, or may be a transgene introduced through genetic engineering techniques.

This invention also covers regenerable cells for use in tissue culture of soybean plant 131TD735. It should be appreciated that the regenerable cells in such tissue cultures include embryos, protoplasts, meristematic cells, callus, pollen, leaves, anthers, pistils, roots, root tips, flowers, seeds, pods or stems. Further aspects and embodiments of the invention are set forth or made evident to one of ordinary skill in the disclosures that follow.

DEFINITIONS

In the description and tables that follow, a number of terms are used. For clarity, and to facilitate an understanding as to the full scope and nature of the invention, the following definitions are provided:

Allele. An allele is any of one or more alternative forms of a gene which relate to one trait or characteristic. In a diploid cell or organism, the two alleles of a given gene occupy corresponding loci on a pair of homologous chromosomes.

Backcrossing. Backcrossing is a process in which a breeder repeatedly crosses hybrid progeny back to one of the parents, for example, a first generation hybrid $F_1$ with one of the parental genotypes of the $F_1$ hybrid.

Brown Stem Rot. This is a visual disease score from 1 to 5 comparing all genotypes in a given test. The score is based on leaf symptoms of yellowing and necrosis caused by brown stem rot. Visual scores range from a score of 1, which indicates no symptoms, to a score of 5 which indicates severe symptoms of leaf yellowing and necrosis.

Cotyledon. A cotyledon is a type of seed leaf. The cotyledon contains the food storage tissues of the seed.

Embryo. The embryo is the small plant contained within a mature seed.

Emergence. This score indicates the ability of the seed to emerge when planted 3" deep in sand at a controlled temperature of 25 degrees C. The number of plants that emerge each day are counted. Based on this data, each genotype is given a 1 to 5 score based on its rate of emergence and percent of emergence. A score of 1 indicates an excellent rate and percent of emergence, an intermediate score of 2.5 indicates average ratings and a 5 score indicates a very poor rate and percent of emergence.

Frogeye Leaf Spot. Primarily a foliar disease of soybean caused by the fungus *Cercospora sojina*. Lesions on leaves are circular to angular spots which vary in size (less than 1 mm to 5 mm in diameter). The lesions are gray to brown spots surrounded by a narrow red or dark reddish-brown margin. The disease can be seedborne. A rating of 1 indicates resistance to frogeye leaf spot infection.

Hilum. This refers to the scar left on the seed that marks the place where the seed was attached to the pod prior to the seed being harvested.

Hypocotyl. A hypocotyl is the portion of an embryo or seedling between the cotyledons and the root. Therefore, it can be considered a transition zone between shoot and root.

Iron-Deficiency Chlorosis. Plants are scored 1 to 5 based on visual observations. A score of 1 means no stunting of the plants or yellowing of the leaves and a score of 5 indicates the plants are dead or dying caused by iron-deficiency chlorosis, a score of 2.5 means plants have intermediate health with some leaf yellowing.

Lodging Resistance. Lodging is rated on a scale of 1 to 5. This is also generally referred to as standability. A score of 1 indicates erect plants. A score of 2.5 indicates plants are leaning at a 45 degree angle in relation to the ground and a score of 5 indicates plants are lying on the ground.

Maturity Date. Plants are considered mature when 95% of the pods have reached their mature color. The number of days is calculated either from days after August 31 or from the planting date.

Maturity Group. This refers to an agreed-on industry division of groups of varieties based on zones in which they are adapted, primarily according to day length or latitude. They consist of very long day length varieties (Groups 000, 00, 0), and extend to very short day length varieties (Groups VII, VIII, IX, X).

Relative Maturity (RM). The term relative maturity is a numerical value that is assigned to a soybean variety based on comparisons with the maturity values of other varieties. The number preceding the decimal point in the RM refers to the maturity group. The number following the decimal point refers to the relative earliness or lateness within each maturity group. For example, a 3.0 is an early group III variety, while a 3.9 is a late group III variety.

Oil or oil percent. Soybean seeds contain a considerable amount of oil. Oil is measured by NIR spectrophotometry, and is reported on an as is percentage basis.

Oleic Acid Percent. Oleic acid is one of the five most abundant fatty acids in soybean seeds. It is measured by gas chromatography and is reported as a percent of the total oil content.

Palmitic Acid Percent. Palmitic acid is one of the five most abundant fatty acids in soybean seeds. It is measured by gas chromatography and is reported as a percent of the total oil content.

*Phytophthora* Resistance. Resistance to *Phytophthora* root rot is rated on a scale of 1 to 5, with a score of 1 being the best or highest tolerance ranging down to a score of 5 which indicates the plants have no tolerance to *Phytophthora*. Also, plant resistance to *Phytophthora* may be determined by the presence or absence of Rsp1 loci.

Phenotypic Score. The Phenotypic Score is a visual rating of general appearance of the variety. All visual traits are considered in the score including healthiness, standability, appearance and freedom of disease. Ratings are scored from 1 being excellent to 5 being poor.

Plant. Plant includes plant cells, plant protoplasts, plant cell tissue cultures which may be used for plant regeneration, plant clumps, and plant cells such as embryos, pollen, ovules, flowers, pods, roots, stems, pistils, leaves, and the like.

Plant Height. Plant height is taken from the top of the soil to the top node of the plant and is measured in centimeters.

Pod. This refers to the fruit of a soybean plant. It consists of the hull or shell (pericarp) and the soybean seeds.

Protein Percent. Soybean seeds contain a considerable amount of protein. Protein is generally measured by NIR spectrophotometry and is reported on an as is percentage basis.

Pubescence. This refers to a covering of very fine hairs closely arranged on the leaves, stems and pods of the soybean plant.

Quantitative Trait Loci (QTL). Quantitative trait loci (QTL) refer to genetic loci that control to some degree numerically representable traits that are usually continuously distributed.

Regeneration. Regeneration refers to the development of a plant from tissue culture.

Seed Protein Peroxidase Activity. Seed protein peroxidase activity refers to a chemical taxonomic technique to separate cultivars based on the presence or absence of the peroxidase enzyme in the seed coat. There are two types of soybean cultivars: those having high peroxidase activity (dark red color) and those having low peroxidase activity (no color).

Seed Yield (Bushels/Acre). The yield in bushels/acre is the actual yield of the grain at harvest.

Seeds per Pound. Soybean seeds vary in seed size, therefore, the number of seeds required to make up one pound also varies. This affects the pounds of seed required to plant a given area and can also impact end uses.

Shattering. The amount of pod dehiscence prior to harvest. Pod dehiscence involves seeds falling from the pods to the soil. This is a visual score from 1 to 5 comparing all genotypes within a given test. A score of 1 means pods have not opened and no seeds have fallen out. A score of 2.5 indicates approximately 50% of the pods have opened, with seeds falling to the ground and a score of 5 indicates 100% of the pods are opened.

Single Gene Converted (Conversion). Single gene converted (conversion) plants refers to plants which are developed by a plant breeding technique called backcrossing wherein essentially all of the desired morphological and physiological characteristics of a variety are recovered in addition to the single gene transferred into the variety via the backcrossing technique or via genetic engineering.

Southern Stem Canker. Caused by *D. phaseolorum* var. *meridionalis*. The first symptoms occur during the early reproductive stages as small, reddish brown lesions, usually near a lower leaf node. As the season progresses, the lesions expand longitudinally to form cankers which are slightly sunken. The stem lesions become long and the leaf symptoms develop with characteristic interveinal chlorosis and necrosis, but no wilting. Foliar symptoms and plant death are caused in part by a phytotoxin.

Soybean Cultivar/Soybean Plant. These terms are used interchangeably throughout. The term generally refers to Glycin max (L). Further, the term generally includes the plant irrespective of breeding method(s) used to create the plant or iterations thereof. For example, the term also encompasses single gene conversions of the variety that is the present invention.

Sudden Death Syndrome. Caused by the soilborne fungus, *Fusarium solani f.* sp. *glycines*. The symptoms first appear on leaves as scattered, interveinal cholortic spots, which may become necrotic or enlarge and form streaks. Leaflets detach from the petioles. The root-mass of infected plants are reduced and discolored and precede foliar symptoms. The infected plants often have increased flower and pod abortion and reduced seed size.

White Mold. Caused by the fungus *Sclerotinia sclerotiorum*. It is a yield limiting disease of soybeans in the north-central United States. It is recognized by white fluffy mycelluim growing on the outside of infected plant stems. The diseased plants wilt, drop their leaves, and turn white or pale tan. Fungus growing on the outside of the stem will produce black sclerotia, which are loosely attached to the stems.

DETAILED DESCRIPTION

Soybean cultivar 131TD735 is an early maturity group III variety with content measured on dry weight basis of protein consisting of 42.0% and oil of 21.1%.

Various other criteria were used in the selective breeding for each generation which criteria included: seed yield, lodging resistance, emergence, disease tolerance, maturity, late season plant intactness, plant height, shattering resistance, and value added characteristics.

Soybean cultivar 131TD735 has demonstrated both stability and uniformity as more fully described below. The cultivar has been self-pollinated a number of generations. Selection from each generation utilized uniformity as a key criteria. The selection criteria and process, and the number of generations used to increase the line has assured the uniformity and stability of Soybean cultivar 131TD735.

Soybean cultivar 131TD735 has the following morphologic and other characteristics.

TABLE 1

VARIETY DESCRIPTION INFORMATION

| | |
|---|---|
| Seed Coat Color (Mature Seed) | Clear |
| Seed Coat Luster (Mature Hand-Shelled Seed) | Dull |
| Cotyledon Color (Mature Seed) | Yellow |
| Leaflet Shape | Ovate |
| Growth Habit | Indeterminate |
| Flower Color | Purple |
| Hilum Color (Mature Seed) | Black |
| Plant Pubescence Color | Tawny |
| Pod Color | Brown |
| Maturity Group | 3 |
| Relative Maturity | 31 |
| Plant Lodging Score (Provide scoring range) | 32 (10-50) |
| Plant Height (cm) | 45 |
| Seed Size (#seeds/lb.) | |
| Seed Content | |
| % Protein | 42.0 |
| % Oil | 21.1 |
| Trypsin Inhibitor Units (TIU) | 18,900 |
| Raffinose + Stachyose (%) | <1.0% |

Methods pertaining to the invention include crossing a first parent and second parent soybean plant, wherein one or both of the parents is the soybean plant from cultivar 131TD735. Any method utilizing soybean cultivar 131TD735 constitutes a part of this invention including selfing, backcrosses, hybrid breeding, and crosses to populations. Any plants produced using soybean cultivar 131TD735 as described above are within the scope of this invention.

The methodology of this invention also encompasses expression vectors introduced into plant tissues using a direct gene transfer method such as microprojectile-mediated delivery, DNA injection, electroporation and the like. Also preferably covered as a part of this invention are expression vectors are introduced into plant tissues by using either microprojectile-mediated delivery with a biolistic device or by using *Agrobacterium*-mediated transformation. Transformant plants obtained with the protoplasm of the invention are intended to be within the scope of this invention.

Table 2 shows similarities and differences between soybean cultivar 131TD735 and another variety.

TABLE 2

COMPARISON WITH OTHER VARIETIES

| Characteristic | 131TD735 | AG2839 |
|---|---|---|
| Flower color | purple | purple |
| Pubescence color | tawny | gray |
| hilum color | Black | imperfect black |
| pod color | brown | brown |
| Sulfonylurea reaction | susceptible | |
| Soybean cyst nematode reaction | resistant | resistant |
| *Phytophthera* reaction | susceptible | resistant |

Further Embodiments of the Invention

Breeding methodology creating transgenes has dramatically evolved over the past years. This methodology customarily involves the construct of a functional expression vector containing DNA comprising one or more genes associated with a promoter or regulator. Transformation vectors may be of a plasmid which alone, or with other plasmids, is utilized to incorporate transgenes into the DNA of the soybean plant. A genetic marker associated with the promoter or other regulator is used to identify and facilitate the predomination of the transformed plant cells either by positive selection or negative selection, or as a reporting marker.

Soybean cultivar 131TD735 is a soybean variety that is the product of a traditional breeding program. The favorable traits result from the use of naturally occurring genes used in breeding soybean cultivar 131TD735. This variety, however, may be created by transgenic methods and, as a result these methods are considered a part of the invention and its disclosure set forth herein.

Any number of genetic markers of bacterial origin are known to exist. See, e.g., Fraley et al., Proc. Natl. Acad. Sci. USA, 80:4803 (1983);. Vanden Elzen et al., Plant Mol. Biol., 5:299 (1985);

Hayford et al., Plant Physiol. 86:1216 (1988), Jones et al., Mol. Gen. Genet., 210:86 (1987), Svab et al., Plant Mol. Biol. 14:197 (1990), Hille et al., Plant Mol. Biol. 7:171 (1986); Comai et al., Nature 317:741-744 (1985); Gordon-Kamm et al., Plant Cell 2:603-618 (1990); and Stalker et al., Science 242:419-423 (1988).

Genetic markers not of bacterial origin are also well known. See, e.g., Eichholtz et al., Somatic Cell Mol. Genet. 13:67 (1987); Shah et al., Science 233:478 (1986); and Charest et al., Plant Cell Rep. 8:643 (1990).

Reporting markers further represent known marking technology. See, e.g., Jefferson, R. A., Plant Mol. Biol. Rep. 5:387 (1987); Teeri et al., EMBO J. 8:343 (1989); Koncz et al., Proc. Natl. Acad. Sci. USA 84:131 (1987); and DeBlock et al., EMBO J. 3:1681 (1984). In vivo and fluorescent marking technologies are known in the art. See, e.g., Molecular Probes publication 2908, IMAGENE GREEN, p. 1-4 (1993); Naleway et al., J. Cell Biol. 115:151a (1991) and Chalfie et al., Science 263:802 (1994).

It is well known in the transformation arts that a nucleotide sequence constitutes the regulator (i.e. Promoter) that drives the genes in an expression vector. There are numerous types of regulators known to the art such as cell-type promoters, tissue-specific promoters, and inducible promoters, all of which are known as non-constitutive promoters. Constitutive promoters are also regulators known in the art. Both constitutive promoters and non-constitutive promoters can be used in the invention disclosed therein. Further discussion regarding these various regulators is found in the following technical literature: Ward et al., Plant Mol. Biol. 22:361-366 (1993) (inducible promoter); Mett et al., Proc. Natl. Acad. Sci. USA 90:4567-4571 (1993)(inducible promoter); Hershey et al., Mol. Gen Genetics 227:229-237 (1991)(inducible promoter); Gatz et al., Mol. Gen. Genetics 243:32-38 (1994)(inducible promoter); Gatz et al., Mol. Gen. Genetics 227:229-237 (1991)(inducible promoter) Schena et al., Proc. Natl. Acad. Sci. USA 88:0421 (1991)(inducible promoter); Odell et al., Nature 313:810-812 (1985)(constitutive promoter); McElroy et al., Plant Cell 2: 163-171 (1990)(constitutive promoter); Christensen et al., Plant Mol. Biol. 12:619-632 (1989)(constitutive promoter); Christensen et al., Plant Mol. Biol. 18:675-689 (1992)(constitutive promoter); Last et al., Theor. Appl. Genet. 81:581-588 (1991)(constitutive promoter); Velten et al., EMBO J. 3:2723-2730 (1984)(constitutive promoter); Lepetit et al., Mol. Gen. Genetics 231:276-285 (1992)(constitutive promoter); Atanassova et al., Plant Journal 2 (3): 291-300 (1992)(constitutive promoter); Murai et al., Science 23:476-482 (1983)(tissue-specific promoter); Sengupta-Gopalan et al., Proc. Natl. Acad. Sci. USA 82:3320-3324 (1985)(tissue-specific promoter); Simpson et al., EMBO J. 4(11):2723-2729 (1985)(tissue-specific promoter); Timko et al., Nature 318:579-582 (1985) (tissue-specific promoter); Twell et al., Mol. Gen. Genetics 217:240-245 (1989) (tissue-specific promoter); Guerrero et al., Mol. Gen. Genetics 244:161-168 (1993) (tissue-specific promoter); and Twell et al., Sex. Plant Reprod. 6:217-224 (1993) (tissue-specific promoter).

Transformative genetics also employ methods to target delivery of the protein produced from a transgerm to a specific subcellular structure, which methods are a part of this invention. Examples of this technology are more fully disclosed in the following technical literature: Becker et al., Plant Mol. Biol. 20:49 (1992); Close, P. S., Master's Thesis, Iowa State University (1993); Knox, C., et al., Plant Mol. Biol. 9:3-17 (1987); Lerner et al., Plant Physiol. 91:124-129 (1989); Frontes et al., Plant Cell 3:483-496 (1991); Matsuoka et al., Proc. Natl. Acad. Sci. 88:834 (1991); Gould et al., J. Cell. Biol. 108:1657 (1989); Creissen et al., Plant J. 2:129 (1991); Kalderon, et al., Cell 39:499-509 (1984); and Steifel, et al., Plant Cell 2:785-793 (1990).

The plants produced by transformative genetics as related to this invention can produce proteins previously unknown to the soybean plant. Such proteins, if commercially useful, are readily obtained by extraction techniques well known in the art. See, e.g., Heney and Orr, Anal. Biochem. 114:92-6 (1981).

Further, agronomic genes can be expressed in the plants transformed pursuant to the present invention. The expression of exemplary genes include, but are not limited to the following disclosures as found in the accompanying technical literature: Jones et al., Science 266:789 (1994); Martin et al., Science 262:1432 (1993); and Mindrinos et al. Cell 78:1089 (1994).

Pest resistance: PCT Application WO 96/30517; PCT Application WO 93/19181. *Bacillus thuringiensis* protein: Geiser et al., Gene 48:109 (1986). A lectin:Van Damme et al., Plant Molec. Biol. 24:25 (1994). Vitamin-binding proteins: PCT application US 93/06487. Enzyme inhibitorsAbe et al., J. Biol. Chem. 262:16793 (1987); Huub et al., Plant Molec. Biol. 21:985 (1993); Sumitani et al., Biosci. Biotech. Biochem. 57:1243 (1993); and U.S. Pat. No. 5,494,813.

Insect-specific hormones or pheromones: Hammock et al., Nature 344:458 (1990).

Insect-specific peptides or neuropeptides: Regan, J. Biol. Chem. 269:9 (1994); Pratt et al., Biochem. Biophys. Res. Comm. 163:1243 (1989); and U.S. Pat. No. 5,266,317.

Insect-specific venoms: Pang et al., Gene 116:165 (1992).

Particularized enzyme—for facilitating cellular accumulation and retention of non-protein molecules with insecticidal activity, etc., or significant to molecular construct modification of a biologically active molecule. See, e.g., PCT application WO 93/02197 (Scott et al.); Kramer et al., Insect Biochem. Molec. Biol. 23:691 (1993); and Kawalleck et al., Plant Molec. Biol. 21:673 (1993).

A Molecular constructs relevant to signal transduction. See, Botella et al., Plant Molec. Biol. 24:757 (1994); and Griess et al., Plant Physiol. 104:1467 (1994).

Molecular constructs significant in the inhabitation of fungal plant pathogens. See, PCT application WO 95/16776.

Molecular constructs confuring disease resistance or protection to the plant. See, e.g., PCT Application WO 95/18855. See, Beachy et al., Ann. Molecular constructs that inhibit it enhance cellular access. See, e.g., Jaynes et al., Plant Sci 89:43 (1993). Molecular constructs that are fatal when ingested by insects. See, e.g., Taylor et al., Abstract #497, Seventh Int'l Symposium on Molecular Plant-Microbe Interactions (Edinburgh, Scotland) (1994).

Naturally occurring parasitic or pathogenic created molecular constructs providing benefit to the plant. See, e.g., Lamb et al., Bio/Technology 10:1436 (1992); Toubart et al., Plant J. 2:367 (1992); Logemann et al., Bio/Technology 10:305 (1992); and Briggs, S., Current Biology, 5(2) (1995).

Molecular constructs conferring protection to the plant against fungus:. See, e.g., Cornelissen and Melchers, Plant Physiol., 101:709-712 (1993); Parijs et al., Planta 183:258-264 (1991) and Bushnell et al., Can. J. of Plant Path. 20(2): 137-149 (1998); and resistance to root rot. See, e.g., Shoemaker et al., *Phytophthora* Root Rot Resistance Gene Mapping in Soybean, Plant Genome IV Conference, San Diego, Calif. (1995).

Genes Producing Molecular Constructs Providing Resistance to Herbicides. Various herbicides can kill the crop producing plant. Thus genes within the crop producing plant that result in the production of molecular constructs that block or otherwise prevent the herbicidal killing mechanisms are beneficial. Examples include, but are not limited to the following references: Lee et al., EMBO J. 7:1241 (1988); Miki et al., Theor. Appl. Genet. 80:449 (1990); U.S. Pat. No. 4,940,835; U.S. Pat. No. 4,769,061; European patent application No. 0 333 033; U.S. Pat. No. 4,975,374; European application No. 0 242 246; DeGreef et al., Bio/Technology 7:61 (1989); Marshall et al., Theor. Appl. Genet. 83:435 (1992); Przibila et al., Plant Cell 3:169 (1991); U.S. Pat. No. 4,810,648; Hayes et al., Biochem. J. 285:173 (1992); Hattori et al., Mol. Gen. Genet. 246:419, 1995; Shiota et al., Plant Physiol., 106:17, 1994; Aono et al., Plant Cell Physiol. 36:1687, 1995; Datta et al., Plant Mol. Biol. 20:619, 1992; U.S. Pat. No. 6,288,306; U.S. Pat. No. 6,282,837; U.S. Pat. No. 5,767,373; and International Publication WO 01/12825.

Genetics Conferring Traits. The general goal of plant breeding is to enhance or introduce traits to the plant that ultimately confer a benefit to humans. Such benefits include increased yield characteristics, increased or decreased oil content, increased or decreased carbohydrate content, and increased or decreased protein content. These benefits may be realized in any numbers of ways, by the introduction of genes that create the desired chemical construct (i.e., increased oleric acid, U.S. Pat. No. 6,063,947, and U.S. Pat. No. 6,323, 392) or decrease an undesired chemical construct (i.e., lowered linilonic acid levels, U.S. Pat. No. 6,969,786. Other examples of desired traits are found in the following references:

Altered fatty acids. U.S. Pat. No. 6,063,947, U.S. Pat. No. 6,323,392, U.S. Pat. No. 6,372,965, U.S. Pat. No. 6,969,786; and Knultzon et al., Proc. Natl. Acad. Sci. USA 89:2625 (1992).

Altered phosphorous content. Van Hartingsveldt, et. al., Gene 127:87 (1993); Raboy et al., Maydica 35:383 (1990).

Altered carbohydrate composition. See, e.g., Shiroza et al., J. Bacteriol. 170:810 (1988) (nucleotide sequence of Streptococcus mutants fructosyltransferase gene); Steinmetz et al., Mol. Gen. Genet. 20:220 (1985); Pen, et. al., Bio/Technology 10:292 (1992) (production of transgenic plants that express Bacillus licheniformis .alpha.-amylase); Elliot, et. al., Plant Molec. Biol. 21:515 (1993) (nucleotide sequences of tomato invertase genes); Sogaard, et. al., J. Biol. Chem. 268:22480 (1993) (site-directed mutagenesis of barley .alpha.-amylase gene); and Fisher, et. al., Plant Physiol. 102:1045 (1993) (maize endosperm starch branching enzyme II).

Altered antioxidant properties. See, e.g., U.S. Pat. No. 6,787,683.

Genes that Control Male Sterility. Introduction of a deacetylase gene under the control of a tapetum-specific promoter and with the application of the chemical N-Ac-PPT. See, International publication WO 01/29237; and U.S. Pat. No. 6,797,864.

Introduction of various stamen-specific promoters. See, WO 92/13956 and WO 92/13957.

Introduction of the barnase and the barstar genes. See, Paul, et al., Plant Mol. Biol. 19:611-622, 1992).

Altering the promoter to prevent the process for transcription of the male fertility gene. U.S. Pat. No. 5,432,068.

Genes Impacting Plant Growth or Agronomic Traits. Various traits may be introduced or introgressed into plants. These traits include flowering, growth, structure and yield. Various examples exist, including U.S. Pat. No. 6,794,560; U.S. Pat. No. 6,307,126; and U.S. Pat. No. 6,713,663.

Genes Impacting Abiotic Stress. The introduction of resistance to abiotic stress is beneficial. These resistant traits are known to include flowering, seed development, drought tolerance, row temperature resistance, and salinity resistance. Examples of the genetics associated with each include: U.S. Pat. No. 5,892,009, U.S. Pat. No. 5,965,705, U.S. Pat. No. 5,929,305, U.S. Pat. No. 5,891,859, U.S. Pat. No. 6,419,428, U.S. Pat. No. 6,664,446, U.S. Pat. No. 6,706,866, U.S. Pat. No. 6,717,034, U.S. Pat. No. 6,084,153, U.S. Pat. No. 6,177, 275, U.S. Pat. No. 6,107,547, U.S. patent application Ser. No. 10/817,483, U.S. patent application Ser. No. 09/545,334, United States Publication No. 2004/0148654, United States Publication No. 2004/0128719, United States Publication No. 2003/0166197, United States Publication No. 2004/ 0098764, and United States Publication No. 2004/0078852.

Methods for Soybean Transformation. A number of transformation protocols exist. See, e.g., Miki et al., "Procedures for Introducing Foreign DNA into Plants" in Methods in Plant Molecular Biology and Biotechnology, Glick, B. R. and Thompson, J. E. Eds. (CRC Press, Inc. Boca Raton, 1993) pages 67-88; and Gruber, et. al., "Vectors for Plant Transformation" in Methods in Plant Molecular Biology and Biotechnology, Glick, B. R. and Thompson, J. E. Eds (CRC Press, Inc., Boca Raton, 1993) pages 89-119, expression vectors and in-vitro culture methods for plant cell or tissue transformation and regeneration.

An expression vector introduction method is based on the natural transformation system of Agrobacterium. See, e.g., Horsch et al., Science 227:1229 (1985); Gruber, et. al., "Vectors for Plant Transformation" in Methods in Plant Molecular Biology and Biotechnology, Glick, B. R. and Thompson, J. E. Eds (CRC Press, Inc., Boca Raton, 1993) pages 89-119;, Moloney, et. al., Plant Cell Reports 8:238 (1989); and U.S. Pat. No. 5,563,055.

A second transformation method involves direct gene transfer. This method may be accomplished in a number of ways: (1) Microprojectile-mediated transformation. See, e.g., Sanford, et. al., Part. Sci. Technol. 5:27 (1987); Sanford, J. C., Trends Biotech. 6:299 (1988); Klein, et. al., Bio/Tech. 6:559-563 (1988); Sanford, J. C. Physiol Plant 7:206 (1990); Klein, et. al., Biotechnology 10:268 (1992); U.S. Pat. No. 5,015, 580; and U.S. Pat. No. 5,322,783. (2) Sonication: See, e.g., Zhang et al., Bio/Technology 9:996 (1991). (3) Fusion: See, e.g., Deshayes, et. al., EMBO J., 4:2731 (1985); Christou, et. al., Proc Natl. Acad. Sci. USA 84:3962 (1987). (4) Direct uptake: Hain, et. al., Mol. Gen. Genet. 199:161 (1985) and Draper et al., Plant Cell Physiol. 23:451 (1982). (5) Electroporation: See, e.g., Donn, et. al., In Abstracts of VIIth International Congress on Plant Cell and Tissue Culture IAPTC, A2-38, p. 53 (1990); D'Halluin, et. al., Plant Cell 4:1495-1505 (1992), and Spencer, et. al., Plant Mol. Biol. 24:51-61 (1994).

A transgenic variety is customarily developed by use of one of the foregoing methods with preferential selection utilizing well known regeneration and selection methods. A new and differing transgenic variety may then be produced by crossing with other varieties. Further, the engineered trait could be transferred to another line by well known backcrossing techniques.

Single-Gene Conversions. These soybean plants are developed by well known backcrossing methods whereby all desired traits, morphological and physiological, are retained while accompanying the single gene transfer into the variety. This methodology is covered by the present invention, the use of which may further improve or introduce a characteristic into the variety. See generally, e.g., Poehlman & Sleper, 1994; and Fehr, 1987; U.S. Pat. No. 5,959,185; U.S. Pat. No. 5,973, 234 and U.S. Pat. No. 5,977,445.

Tissue Culture. This method of reproduction is applicable to tissues of soybeans, and is well known. See, e.g., Komatsuda, T. et al., Crop Sci. 31:333-337 (1991); Stephens, P. A., et. al., Theor. Appl. Genet. (1991) 82:633-635; Komatsuda, T. et. al., Plant Cell, Tissue and Organ Culture, 28:103-113 (1992); Dhir, S. et. al., Plant Cell Reports (1992) 11:285-289; Pandey, P. et. al., Japan J. Breed. 42:1-5 (1992); Shetty, K., et. al., Plant Science 81:245-251 (1992); U.S. Pat. No. 5,024, 944; and U.S. Pat. No. 5,008,200. This invention includes the provision of cellular material which may be used to develop soybean plants having the physiological and morphological characteristics of soybean cultivar 131TD735.

General Breeding Methods. Soybean cultivar 131TD735, developed for grain and seed production, may also be used to provide a source of breeding material used to develop new soybean varieties. Plant breeding techniques well known in a soybean plant breeding program include recurrent selection, mass selection, bulk selection, backcrossing, pedigree breeding, restriction fragment length polymorphism enhanced selection, genetic marker enhanced selection, making douple haploids, and transformation. Combinations of techniques may be used. Generally, a soybean variety plant breeding program involves the development and evaluation of homozygous varieties. Many analytical methods are well known for developmental evaluation, with the historic approach focusing on observable phenotypic traits. Genotypic analysis may also be used.

Breeding Methodologies Using Soybean Cultivar 131TD735. This invention specifically includes methods for producing a soybean plant by crossing a first parent soybean plant with a second parent soybean plant with one or both of the parent plants being cultivar 131TD735. All plants produced using soybean cultivar 131TD735 as at least one parent are within the scope of this invention, including those plants developed from cultivars derived from soybean cultivar 131TD735. Any of the breeding methods described within this specification are part of this invention. Certain of the common and well known breeding methods are below discussed.

Pedigree Breeding. Two genotypes, such as cultivar 131TD735 and another soybean variety with desirable characteristics addition or complimentary to the traits of cultivar 131TD735, are crossed. Additional exhibiting desired traits may be used in the selection process. Superior plants are selfed and selected in successive filial generations, with a homogenous variety resulting from the self-pollination and selection. Backcrossing may be used in combination with pedigree breeding. Therefore, an embodiment of this invention is a method of making a backcross conversion of a soybean cultivar 131TD735 comprising the steps of crossing a plant of soybean cultivar 131TD735 with a donor plant comprising a desired trait, selecting an F1 progeny plant comprising the desired trait, and backcrossing the selected F1 progeny plant to a plant of soybean cultivar 131TD735 and using the molecular marker profile to select for a progeny plant with the desired trait and the molecular marker profile of cultivar 131TD735. In one embodiment the desired trait is a mutant gene or transgene present in the donor parent.

Recurrent Selection. Soybean cultivar 131TD735 is useful in a recurrent selection program. Individual plants are cross pollinated with each other to form progeny. The progeny are grown, and the superior progeny selected by known selection methods which generation is then cross pollinated with each other to form progeny for another population. Recurrent selection is cyclical and may be repeated any number of times with the objective being to improve the traits of a population. The improved population is then available for use as a source of breeding material to obtain new varieties.

Mass selection. This method involves the selection of seeds based upon desired traits which are bulked and planted. Mass selection is a useful technique when used in conjunction with molecular marker enhances selection. In mass selection seeds from individuals are selected based on performance or composition so as to grow the next generation. Seeds from successive generations are used to grow successive generations, the selection of which is based upon the use of sampling techniques, This method customarily uses molecular marker enhanced selection.

Mutation Breeding. Soybean cultivar 131TD735 may also be used in mutation breeding. Mutations that occur spontaneously or artificially provide a source of variability. Artificial mutagenesis increases the rate of mutation for a desired characteristic, and may be accomplished by means that include temperature, long-term seed storage, tissue culture conditions, radiations or chemical mutagens. Each mutated line is observed for purposes of identifying a modified trait that may be deemed as beneficial, which trait may then be incorporated by well known breeding methods. See, e.g., "Principles of Cultivar Development" Fehr, 1993, Macmillan Publishing Company. Other mutated soybean plants may also be used to produce a backcross conversion of soybean cultivar 131TD735 that comprises such mutation.

Molecular Markers Breeding. Molecular markers identified through techniques such as Isozyme Electrophoresis, Restriction Fragment Length Polymorphisms (RFLPs), Randonly Amplified Polymoprhic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) and Single Nucleotide Polymorphisms (SNPs), may be used in plant breeding methods utilizing soybean cultivar 131TD735.

Production of Double Haploids. Doubling of a set of chromosomes (1 N) from a heterozygous plant to produce a completely homozygous individual is generally referred to as double haploid production. This method is beneficial in speeding the breeding process by eliminating generations of selfing required to obtain a homozygous plant. See, e.g., Coe, 1959, *Am Nat.* 93:381-382; Sharkar and Coe, 1966, *Genetics* 54:453-464; Deimling, Roeber, and Geiger, 1997, *Vortr. Pflanzenzuchtg* 38:203-224; Chalyk, Bylich & Chebotar, 1994, MNL 68:47; Chalyk & Chebotar, 2000, Plant Breeding 119:363-364; Kermicle 1969 *Science* 166:1422-1424.

An embodiment on this invention is a process for making a substantially homozygous 131TD735 progeny by use of the double haploid methods. Methods for obtaining haploid plants are disclosed in any number of references including: Kobayashi, M., et. al., *Journ. Of Heredity* 71(1):9-14, 1980, Pollacsek, M., Agronomie (Paris) 12(3):247-251, 1992; Cho-Un-Haing et al., *Journ. Of Plant Biol.*, 1996, 39(3): 185-188; Verdoodt, L., et. al., February 1998, 96(2):294-300; Genetic Manuipulation in Plant Breeding, Proceedings International Symposium Organized by EUCARPIA, Sep. 8-13, 1985, Berlin, Germany; Chalyk, et. al., 1994, Maize Genet Coop. Newsletter 68:47; Chalys, S.; Bernardo, R. and Kahler, A. L., Theor. Appl. Genet. 102:986-992, 2001.

INDUSTRIAL USES

The seed of soybean cultivar 131TD735, the plant produced from the seed, the hybrid soybean plant produced from the crossing of the variety with any other soybean plant, hybrid seed, and various parts of the hybrid soybean plant may be utilized for human food, livestock feed, as a raw material in industry, or may provide a feedstock for energy production or lubricating products. The oil and meal of cultivator 131TD735, including flour and other products thereof, are a part of this invention.

TABLES

In Table 3 that follows, the traits and characteristics of soybean cultivar 131TD735 are compared to other varieties of commercial soybeans of similar maturity. In Table 3, column 1 shows the variety, column 2 shows the test year, column 3 shows the number of locations, column 4 shows the number of observations, and column 5 shows the mean yield in bushels per acre.

TABLE 3

| Cultivar | Year | # of locs | # of obs | Yield |
| --- | --- | --- | --- | --- |
| 131TD735 | 2010 Summer | 7 | 7 | 51.9 |
| AG2839 | 2010 Summer | 7 | 7 | 55.6 |

DEPOSIT INFORMATION

A deposit of the Schillinger Genetics, Inc. proprietary soybean cultivar designated 131TD735 disclosed above and recited in the appended claims has been made with the National Collections of Industrial, Food and Marine Bacteria (NCIMB), Ferguson Building, Craibstone Estate, Bucksburn, Aberdeen, Scotland AB21 9YA. The deposit was accepted on Aug. 9, 2012. The deposit of 2,500 seeds was taken from the same deposit maintained by Schillinger Genetics, Inc. All restrictions upon the deposit have been removed, and the deposit is intended to meet all of the requirements of 37 C.F.R. 1.801-1.809. The NCIMB accession number is NCIMB 42025. The deposit will be maintained in the depository for a period of 30 years, or 5 years after the last request, or for the effective life of the patent, whichever is longer, and will be replaced as necessary during that period.

All publications, patents, and patent applications mentioned in the specification reflect, but do not necessarily limit information generally known in the art and appreciated by those skilled in the art. All such references, individually, are incorporated by reference herein.

Having thus described the invention in connection with the preferred embodiments thereof, it will be evident to those skilled in the art that various revisions can be made to the preferred embodiments described herein without departing from the spirit, concept, and scope of the invention.

What is claimed is as follows:

1. A seed of soybean cultivar 131TD735, wherein a representative sample of seed of said cultivar was deposited under NCIMB Accession No. 42025.

2. A soybean plant, or a part thereof, produced by growing the seed of claim 1.

3. A tissue culture of cells produced from the plant of claim 2, wherein said cells of the tissue culture are produced from a plant part selected from the group consisting of leaf, pollen, embryo, cotyledon, hypocotyl, meristematic cell, root, root tip, pistil, anther, flower, stem, pod and petiole.

4. A protoplast produced from the plant of claim 2.

5. A protoplast produced from the tissue culture of claim 3.

6. A soybean plant regenerated from the tissue culture of claim 3, wherein the plant has all of the morphological and physiological characteristics of cultivar 131TD735.

7. A method for producing an $F_1$ hybrid soybean seed, wherein the method comprises crossing the plant of claim 2 with a different soybean plant and harvesting the resultant $F_1$ hybrid soybean seed.

8. A F1 hybrid soybean seed produced by the method of claim 7.

9. A F1 hybrid soybean plant, or a part thereof, produced by growing said hybrid seed of claim 8.

10. A method of producing an herbicide resistant soybean plant wherein the method comprises transforming the soybean plant of claim 2 with a transgene wherein the transgene confers resistance to an herbicide selected from the group consisting of imidazolinone, sulfonylurea, glyphosate, glufosinate, L-phosphinothricin, triazine and benzonitrile.

11. An herbicide resistant soybean plant produced by the method of claim 10.

12. A method of producing an insect resistant soybean plant wherein the method comprises transforming the soybean plant of claim 2 with a transgene that confers insect resistance.

13. An insect resistant soybean plant produced by the method of claim 12.

14. The soybean plant of claim 13, wherein the transgene encodes a Bacillus thuringiensis endotoxin.

15. A method of producing a disease resistant soybean plant wherein the method comprises transforming the soybean plant of claim 2 with a transgene that confers disease resistance.

16. A disease resistant soybean plant produced by the method of claim 15.

17. A method of producing a soybean plant with modified fatty acid metabolism, modified carbohydrate metabolism, or decreased phytate content, wherein the method comprises transforming the soybean plant of claim 2 with a transgene encoding a protein selected from the group consisting of phytase, fructosyltransferase, levansucrase, alpha-amylase, invertase and starch branching enzyme or transforming a plant with an antisense gene of stearyl-ACP desaturase.

18. A soybean plant having modified fatty acid metabolism or modified carbohydrate metabolism produced by the method of claim 17.

19. A method of introducing a desired trait into soybean cultivar 131TD735 wherein the method comprises: a. crossing a 131TD735 plant, wherein a representative sample of seed was deposited under NCIMB Accession No. 42025, with a plant of another soybean cultivar that comprises a desired trait to produce progeny plants wherein the desired trait is selected from the group consisting of male sterility, herbicide resistance, insect resistance, modified fatty acid metabolism, modified carbohydrate metabolism, or decreased phytate content, modified seed yield, modified oil percent, modified protein percent, modified lodging resistance, modified shattering, modified iron-deficiency chlorosis and resistance to bacterial disease, fungal disease or viral disease; b. selecting one or more progeny plants that have the desired trait to produce selected progeny plants; c. crossing the selected progeny plants with the 131TD735 plants to produce backcross progeny plants; d. selecting for backcross progeny plants that have the desired trait and all of the physiological and morphological characteristics of soybean cultivar 131TD735 listed in Table 1; and e. repeating steps (c) and (d) three or more times in succession to produce selected fourth or higher backcross progeny plants that comprise the desired trait and all of the physiological and morphological characteristics of soybean cultivar 131TD735 listed in Table 1.

20. A soybean plant produced by the method of claim 19, wherein the plant has the desired trait and all of the physiological and morphological characteristics of soybean cultivar 131TD735 listed in Table 1.

21. The soybean plant of claim 20, wherein the desired trait is herbicide resistance and the resistance is conferred to an herbicide selected from the group consisting of imidazolinone, sulfonylurea, glyphosate, glufosinate, L-phosphinothricin, triazine and benzonitrile.

22. The soybean plant of claim 20, wherein the desired trait is insect resistance and the insect resistance is conferred by a transgene encoding a Bacillus thuringiensis endotoxin.

23. The soybean plant of claim 20, wherein the desired trait is modified fatty acid metabolism, modified carbohydrate metabolism, or decreased phytate content, and said desired trait is conferred by a nucleic acid encoding a protein selected from the group consisting of phytase, fructosyltransferase, levansucrase, alpha-amylase, invertase and starch branching enzyme or transforming a plant with an antisense gene of stearyl-ACP desaturase.

* * * * *